United States Patent [19]

Kajiyama

[11] 4,389,894
[45] Jun. 28, 1983

[54] CYLINDRICAL GUIDE RAIL FOR DETECTOR

[75] Inventor: Shigeru Kajiyama, Hitachi, Japan

[73] Assignees: Hitachi Ltd.; Babcock-Hitachi Kabushiki Kaisha, both of Tokyo, Japan

[21] Appl. No.: 229,841

[22] Filed: Jan. 30, 1981

[30] Foreign Application Priority Data

Jan. 30, 1980 [JP] Japan ..................................... 55-8819

[51] Int. Cl.³ ............................................ G01N 29/04
[52] U.S. Cl. ....................................................... 73/637
[58] Field of Search ................. 73/622, 637, 638, 640; 324/261

[56] References Cited

U.S. PATENT DOCUMENTS 3,248,933 5/1966 Stebbins ................................ 73/640
3,921,440 11/1975 Toth ...................................... 73/622
4,331,034 5/1982 Takeda et al. ........................ 73/637

FOREIGN PATENT DOCUMENTS 52-108874 9/1977 Japan ..................................... 73/637

Primary Examiner—Stephen A. Kreitman
Attorney, Agent, or Firm—Antonelli, Terry & Wands

[57] ABSTRACT

An ultrasonic flaw detector is guided around a cylindrical pipe to be inspected by a cylindrical guide rail which is in the form of a split circular ring with a latch and a hinge. On the inner surface of the ring, geared bridge jacks are provided to secure the rings around the outer peripheral surface of the pipe. The ring is mounted to the peripheral surface of the pipe by turning a flexible wire rod connecting respective screws of the jacks. On the outer surface of the rings, a circular guide track and rack are arranged for engagement with the flaw detector.

10 Claims, 4 Drawing Figures

CYLINDRICAL GUIDE RAIL FOR DETECTOR

BACKGROUND AND SUMMARY OF THE INVENTION

The present invention relates to a cylindrical guide rail for guiding nondestructive flaw detector and more particularly to a clamping device for securing the cylindrical guide rail aroung a cylindrical object to be inspected such as a pipe.

In the case of nuclear power plant, various regulations are provided which require periodical inspections of pipes or nozzles by using a nondestructive detector such as an ultrasonic flaw detector. Generally, those inspections are accomplished by manipulating the detector around the object to be inspected from a remote location to prevent operators from radiation damage. The detector is manipulated circumferencially and axially around the pipe by remote control along a cylindrical guide rail which is secured around the surface of the object. In order to perform inspections accurately, the guide rail must be clamped to the object securely. Also, the guide rail must be mounted and dismounted in as short time as possible to minimize the radiation damage of the operator, because mounting and dismounting operations can not be performed by remote control. Further, the guide rail must be adjustable for various size of pipes, because there are so many pipes in the plant, which have various size in diameter.

Various clamp mechanisms have been proposed to secure the guide rail around the pipe, for example, in the U.S. Pat. No. 3,921,440, an inflatable bladder is arranged between inner surfaces of the guide rail and outer periferal surfaces of the pipe. However, this type of bladder is not duarable for a pipe of high temperature. Another known clamping mechanism is to provide a plurality of clamp screws around the guide rail, which are adjustably extending in the radial direction toward the pipe. However, as each clamp screw must be adjusted independently, it is difficult to secure the guide rail coaxially about the cylindrical pipe. Also, it takes long to mount or dismount the guide rail as there are so many clamp screws necessary.

It is therefore an object of the present invention to provide an improved cylindrical guide rail which can be mounted and dismounted for a shorter operating period with simple and duarable mechanisms.

According to a preferred embodiment of the present invention, a split cylindrical ring which has a plurality of adjustable jacks circumferencially around the inner peripheral surface of the ring is obtained. Each jack adjustably moves respective clamp shoes provided on the jack in the radial direction of the ring so as to clamp a circular object to be inspected. Each jack is connected by a single force transmitting means through which the adjustment of respective clamp shoes is attained.

Because of a simple clamp mechanism, the weight of the guide rail has advantageously reduced. Further, as each jack is connected by the force transmitting means and the adjustment of the respective clamp shoes can be made by a single operation of the force transmitting means, the clamp operation is advantageously shortened and the adjustment of the guide rail in the axis of the object has remarkably made easier.

Also, by the use of jacks for the clamp mechanism, clamp force required has remarkably reduced and no special tool for the clamp operation is necessary.

The clamp mechanism of the present invention is especially preferred in case where the diameter of the object to be inspected varies in a large extent.

Further objects and advantages of the present invention will be explained with reference to the following drawings.

DETAILED DESCRIPTION OF DRAWINGS

Figure 1:
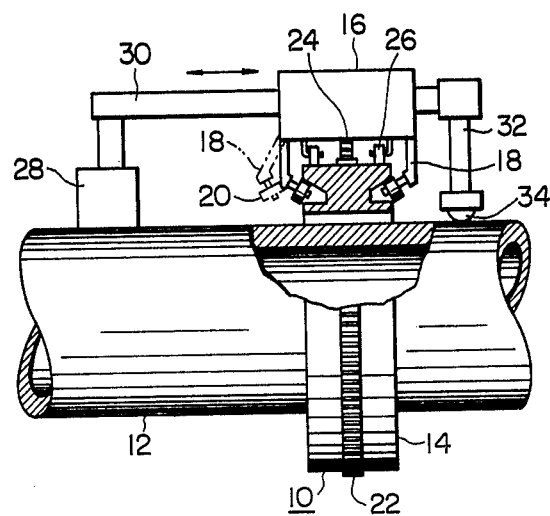
FIG. 1 is a partially broken horizontal elevational view of a guide rail secured around a pipe to be inspected.

FIG. 1 shows an overall view of the present invention in which the cylindrical guide rail 10 is clamped to a pipe 12 to be inspected. The guide rail 10 has circumferencial guide tracks 14 at respective side faces of the guide rail 10 along which a drive unit 16 is guided. A pair of guide legs 18 having rollers 20 are provided at both sides of the drive unit 16 for adaption to the circular guide tracks 14. These guide legs 18 are movable as illustrated by the dotted line in the case of dismounting of the drive unit 16. The guide rail 10 also has a circumferencial gear rack 22 on the outer peripheral surface of the guide rail 10, which mates a pinion geare 24 on the drive unit 16. The drive unit 16 is also supported by a pair of support roller 26 on the outer peripheral surface of the guide rail 16. The drive unit 16 has a drive motor (not shown) connected to the pinion gear 24, through which the drive unit 16 is driven circumferencially along the gear rack 22.

A search head 28 of the detector is secured at one end of a manipulator arm 30 which is supported by the drive unit 16. The drive unit 16 has a driving mechanism which is adapted to move the manipulator arm 30 longitudinally in relation to the longitudinal axis of the circular pipe 12. Another end of the manipulator arm has a guide arm 32 with a roller 34 to secure the search head 28 on the pipe surface. Inspection of the circular pipe 12 is completed in this way by manipulating the search head 28 of the detector axially and circumferentially around the pipe 12. As the movement of the manipulator in the longitudinal direction is limited, the guide rail is dismounted from the pipe 12 after completion of the inspection and remounted to another place of the pipe 12 where inspection will be made. The details of the clamp mechanism of the guide rail will be explained with reference to FIG. 2.

Figure 2:
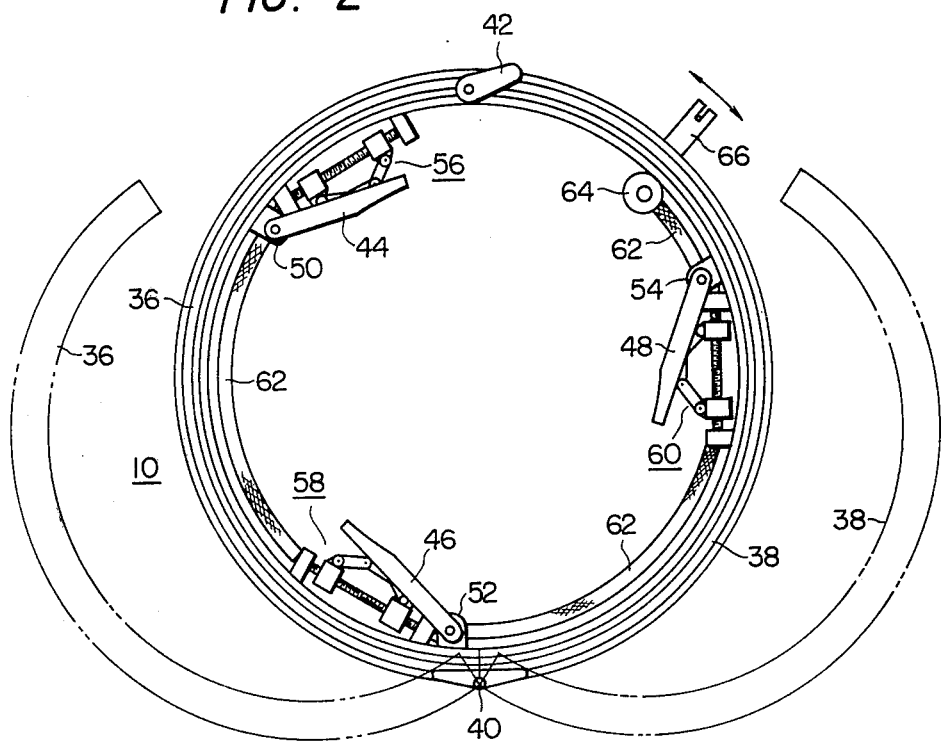
FIG. 2 is a side elevational view of the guide rail as shown in FIG. 1.

FIG. 2 shows a preferred embodiment of the guide rail 10 of the present invention. The guide rail is formed of a pair of semi-circular rings 36 and 38 connected together at one end of respective rings by a hinge 40, so that the guide rail 10 may be mounted around the pipe 12 in the closed position. The other ends of respective rings are arranged to engage each other and form a complete circular guide rail 10 when mounted around the pipe in the closed form. The emgagement of the respective ends of the rings 36 and 38 are easily secured by any suitable means such as a latch 42. Clamp shoes 44, 46 and 48 are pivotally secured at one ends respectively to base plates 50, 52 and 54 arranged on the inner surface of the rings 36 and 38 preferably with an equal distance to each other. The other end portions of respective clamp shoes 44, 46 and 48 are supported by jacks 56, 58 and 60. The jack has a thread rod and link bridges to support and lift the clamp shoes in the radial direction of the rings 36 and 38. Each thread rod of the jacks is connected in series by a flexible rod 62 such as wire rope arranged along the inner peripheral surface of the guide rail 10. One end of the flexible rod 62 is connected to a bevel pinion 64. A ratchet handle 66 is connected to a bevel gear (not shown) engaging the bevel pinion 64. The clamp shoes 44, 46 and 48 are lifted toward the outer peripheral surface of the pipe to be inspected and clamp the guide rail 10 around the pipe by turning the ratchet handle 66 back and forth as shown by the arrow. The ratchet handle is socketed on a shaft of the bevel gear and is easily detachable. By turning a switch lever (not shown) of the ratchet handle 66, the turning direction of the wire rope 62 is changed and the clamp shoes are released from the outer peripheral surface of the pipe.

Figure 3:
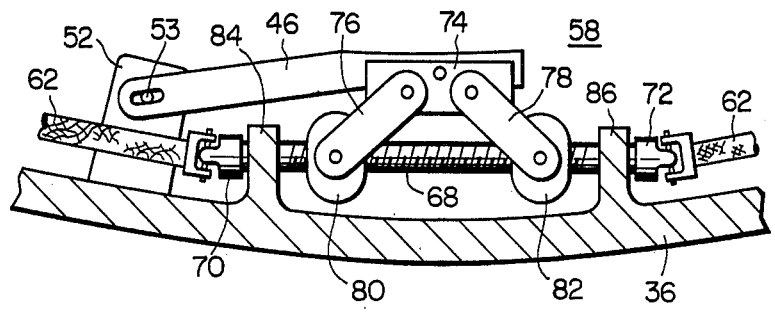
FIG. 3 is an enlarged view of a clamping device of the guide rail as shown in FIG. 2.

Hereafter, the clamp mechanism 58 of FIG. 2 will be explained more in detail with reference to FIG. 3. The wire rope 62 is connected to respective ends of a screw rod 68 through universal couplings 70 and 72 so that the rotation of the wire rope 62 is transmitted to the screw rod 68 without twisting the wire rope 62. The rotation is further transmitted to the clamp mechanism 56 in FIG. 2. The clamp shoe 46 is swingably supported at one end by a pin 53 on the base plate 52 secured to the ring 36. Another end portion of the clamp shoe 46 is joined to a support plate 74 which is supported by a pair of link arm 76 and 78. The link arms 76 and 78 are pin-joined respectively to screw nuts 80 and 82 through which the screw rod 68 is engaging. Both ends of the screw rod are supported by bearings 84 and 86. As, the screw nuts 80 and 82 have threads of different angles, by turning the ratchet handle 66, the screw nuts 80 and 82 move opposite directions along the screw rod 68 so as to move the clamp shoe 46 connected by the link arms 76 and 78 unwardly or downwardly upon the turning direction of the wire rope 62. In this embodiment, the clamp shoe 46 is swingably supported by the base plate 52, however, if the rotation of the screw nuts 80 and 82 can be prevented by some other means, the clamp shoe 46 is not always necessary and the support plate 74 can substitute for the clamp shoe 46. In this case, the support plate 74 is pressed against the outer perepheral surface of the pipe to be inspected by the clamp mechanism 58. Also, one of the link arms 76 or 78 is not always necessary, because the clamp shoe 46 can act as a link arm.

Figure 4:
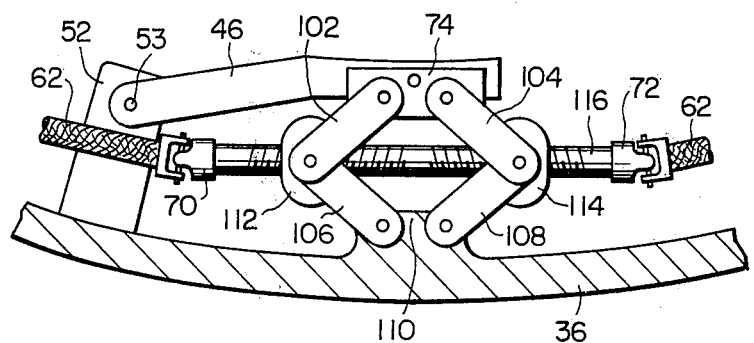
FIG. 4 is an enlarged view of a clamping device according to another embodiment of the invention.

Another embodiment of the clamp mechanism will be explained with reference to FIG. 4 in which the clamp shoe 46 is supported by four link arms 102, 104, 106 and 108. The link arms 102 and 104 are supporting the support plate 74 the same way as the embodiment shown in FIG. 3. The other ends of the link arms 102 and 104 are respectively pin-joined to screw nuts 112 and 114. Also, link arms 106 and 108 are pin-joined to the screw nuts 112 and 114 respectively. The other ends of the link arms 106 and 108 are swingably supported to a base 110 of the ring 36. A screw rod 116 which is coupled to the wire rope 62 through universal couplings 70 and 72 is engaging with the screw nuts 112 and 114. The screw rod 116 has a right angle thread on one side and a left angle thread on another. On the other hand, the screw nuts 112 and 114 have threads of the same angle. By turning the ratchat handle 66, the screw nuts 112 and 114 move opposite directions along the screw rod 116 and the clamp shoe 46 connected to the link arms 102 and 104 upwardly or downwardly. According to the present embodiment in FIG. 4, both the upper link arms (102 and 104) and the lower link arms (106 and 108) move in response to the rotation of the screw rod 116, larger movement of the clamp shoe 46 in the radial direction can be obtained as compared with the embodiment shown in FIG. 3. In this embodiment, the screw rod 116 has threads of different angles, however, the embodiment is not limited to the drawing and the screw rod as shown in FIG. 3 can be applicable.

What is claimed is:

1. A cylindrical guide rail for a detector having; a split cylindrical ring, each half ring being hinged together, guide means provided circumferencially around said split ring, along which the detector being driven, a plurality of clamp shoes arranged around the inner surface of said split ring for securing said split ring in the closed position coaxially around a cylindrical object to be inspected, adjusting means for adjusting positions of said clamp shoes toward and away from the cylindrical object to be inspected, wherein the improvement comprising; jack means secured to the inner surface of said split ring and supporting said clamp shoes for adjusting the positions of said clamp shoes, force transmitting means provided circumferentially around the split ring for transmitting a force to each of said jack means, thereby the force applied is transmitted to said respective jack means and converted into a force to adjust the positions of said respective clamp shoes.

2. A cylindrical guide rail according to claim 1, wherein said force transmitting means comprises a flexible rod which can transmit a rotational force to said respective jack means, and said jack means comprises link means arranged to lift said clamp shoes toward and away from the object to be inspected by the rotational force transmitted through said flexible rod.

3. A cylindrical guide rail according to claim 2, wherein one end of said link means is joined to said clamp shoes and another end is engaged with a screw rod coupled to said flexible rod.

4. A cylindrical guide rail according to claim 3, wherein said link means are formed of at least a pair of link arms, said arms are forming a bridge to support said clamp shoes at one end of respective arms, and another end of respective arms are engaging said screw rod such that said clamp shoes are moved in the radial direction of said split ring by turning said flexible rod.

5. A cylindrical guide rail according to claim 4, wherein one end of said arms is pin-joined to a nonrotating nut engaging to said screw rod.

6. A cylindrical guide rail according to claim 2 or 3 or 4 or 5, wherein said flexible rod comprising a flexible wire rod.

7. A cylindrical guide rail according to claim 3 or 4 or 5, wherein said force transmitting means is coupled to respective ends of said screw rod by universal couplings.

8. A cylindrical guide rail according to claim 2 or 3 or 4 or 5, wherein the rotational force of the flexible rod is transmitted through a ratchet handle provided at the end of said flexible rod.

9. A cylindrical guide rail according to claim 4 or 5, wherein said screw rod has a right angle screw at one side and a left angle screw at another side.

10. A cylindrical guide rail according to claim 1 or 2 or 3 or 4 or 5, wherein one end of said clamp shoes is pin-joined to said ring and another end portion is pin-joined to said jack means.

* * * * *